United States Patent [19]
Peters et al.

[11] Patent Number: 5,916,888
[45] Date of Patent: Jun. 29, 1999

[54] IMIDAZO[1,5A]PYRIDINE DERIVED SERINE PROTEASE INHIBITORS

[75] Inventors: Jacobus Albertus Maria Peters, Oss; Henricus Carl Joseph Ottenheym, Milsbeek; Anton Egbert Peter Adang, Eindhoven, all of Netherlands

[73] Assignee: Akzo Nobel, N.V., Arnhem, Netherlands

[21] Appl. No.: 08/973,255

[22] PCT Filed: May 29, 1996

[86] PCT No.: PCT/EP96/02298

§ 371 Date: Dec. 2, 1997

§ 102(e) Date: Dec. 2, 1997

[87] PCT Pub. No.: WO96/38470

PCT Pub. Date: Dec. 5, 1996

[30] Foreign Application Priority Data

Jun. 2, 1995 [EP] European Pat. Off. .............. 95201448

[51] Int. Cl.⁶ .......................... C07K 5/02; C07D 471/04; A61K 38/55
[52] U.S. Cl. ................. 514/212; 514/2; 514/19; 540/524; 546/121
[58] Field of Search ............... 540/524; 546/121; 514/212, 300, 2.19

[56] References Cited

FOREIGN PATENT DOCUMENTS 0335483  10/1989  European Pat. Off. .

OTHER PUBLICATIONS

C. Klein et al., *Liebigs Annalen Der Chemie*, 9:1623–1637, 1983.
R. Gonzalez–Muniz et al., *Tetrahedron*, 48:24:5191–5198, 1992.

*Primary Examiner*—Richard L. Raymond
*Attorney, Agent, or Firm*—Mary E. Gormley

[57] ABSTRACT

The invention relates to an imidazole[1,5a]pyridine derived serine protease inhibitor comprising a unit having general formula (I)

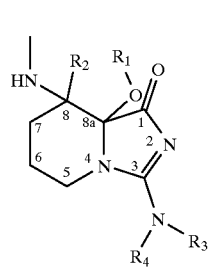

(I)

wherein $R_1$ is hydrogen, lower alkyl or an acyl group; $R_2$ is hydrogen or lower alkyl; $R_3$ and $R_4$ are independently hydrogen, lower alkyl or together form $=CH-NR_5NR_6$, $R_5$ and $R_6$ being lower alkyl. The compounds are serine protease inhibitors and can be used for the treatment and prophylaxis of thrombosis and thrombin-associated diseases.

17 Claims, No Drawings

IMIDAZO[1,5A]PYRIDINE DERIVED SERINE PROTEASE INHIBITORS

This application is a 371 of PCT/EP96/02298, filed May 29, 1996.

FIELD OF THE INVENTION

The invention relates to imidazo[1,5a]pyridine derived serine protease inhibitors, a process for the preparation thereof, a pharmaceutical composition containing the same, as well as the use of these imidazo[1,5a]pyridine derived serine protease inhibitors for medical therapy, and in particular for treating and preventing of thrombosis or other thrombin associated diseases.

BACKGROUND OF THE INVENTION

Imidazo[1,5]pyridine derivatives are known, for instance 3-amino-6,7,8,8a-tetrahydro-8a-hydroxyimidazo[1,5a]pyridin-1(5H)-one is described by Klein et al. (Liebigs Ann. Chem. 1623–1637, 1983). No pharmacological activity is disclosed for this compound.

The 8-substituted 3,8-diamino-imidazo[1,5a]pyridin-1(5H)-one derivatives of the present invention are novel compounds which are selective reversible inhibitors of serine proteases that require a basic amino acid residue at the $P_1$ position of their substrates.

The invention relates to imidazol[1,5a]pyridine derived serine protease inhibitors comprising a unit having the general formula I

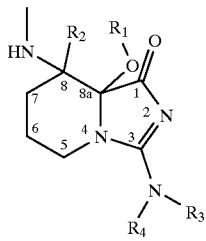

wherein $R_1$ is hydrogen, lower alkyl or an acyl group; $R_2$ is hydrogen or lower alkyl; $R_3$ and $R_4$ are independently hydrogen, lower alkyl or together form $=CH-NR_5R_6$, $R_5$ and $R_6$ being lower alkyl; or a pharmaceutically acceptable salt thereof.

In the definition of the compounds of formula I the term lower alkyl means a branched or unbranched alkyl group having preferably 1–6 carbon atoms, like hexyl, isobutyl, propyl, isopropyl, ethyl, and, most preferred, methyl.

The term acyl group means a 1-oxoalkyl group derived from carboxylic acid having from 1 to 6 carbon atoms, like hexanoyl, tert-butanoyl, propionyl, acetyl and formyl. The preferred acyl group is the acetyl group.

The serine proteases are a class of proteolytic enzymes that catalyze the hydrolysis of specific peptide bonds in proteinaceous substrates. Schechter and Berger (Biochem. Biophys. Res. Commun. 27, 157–162, 1967) have proposed a now often used nomenclature for the identification of amino acid residues in the substrates of the serine proteases:

Substrate: ~=scissile bond
... $P_n$ ... $P_4$-$P_3$-$P_2$-$P_1$~$P_1'$-$P_2'$-$P_3'$-$P_4'$ ... $P_n'$ ...
Enzyme:
... $S_n$ ... $S_4$-$S_3$-$S_2$-$S_1$-$S_1'$-$S_2'$-$S_3'$-$S_4'$ ... $S_n'$ ...

The amino acid residues of the subsites of the substrate at the N-terminus of the scissile $P_1$-$P_1'$ bond are designated $P_1$, $P_2$ etc. and as $P_1'$, $P_2'$ etc. at the C-terminus. These subsites of the substrate correspond to the possible subsites ($S_1$, $S_2$, etc) on the enzyme with which the binding interactions take place.

The compounds of the present invention are inhibitors of the serine proteases that require a basic amino acid residue, like arginine or lysine, at the $P_1$ position of their substrates. Representative examples of these serine proteases are trypsin, plasmin, urokinase plasminogen activator, kallikreins, calpain, acrosin, and thrombin.

The present invention provides analogues of peptide substrates, which encompass residues from the P-region of substrates of the pertinent proteases only, in which the terminal $P_1$-residue is replaced by the 3,8-diamino-imidazo[1,5a]pyridin-1(5H)-one unit of formula I.

It is a major goal of the present invention to provide selective inhibitors of certain serine proteases that form part of the blood clotting cascade. In this enzymatic cascade the activated form of one clotting factor catalyzes the activation of the next factor, ultimately leading to the rapid generation of the arginine-directed ($P_1$ substrate residue is an arginine) serine protease thrombin (factor IIa) from its precursor prothrombin (factor II). The latter process is catalyzed by factor Xa, which is also an arginine-directed serine protease. Thrombin, the last enzyme in the coagulation system, will cleave the soluble plasma protein fibrinogen to generate fibrin monomers, which are cross-linked to form an insoluble gel. Apart from being involved in the regulation of its own production and activity, thrombin is a potent platelet agonist, thereby inducing platelet aggregation. Activated platelets form together with the fibrin polymer matrix and entrapped erythrocytes the blood clot or thrombus.

Thrombin plays a key role in the process of haemostasis, the physiological process which arrests bleeding from an injured blood vessel. It also plays a role in thrombosis, which is the pathological condition whereby inappropriate activity of the haemnostatic mechanism results in the formation of intravascular thrombi, which in turn lead to interruption of blood flow. Thrombosis can occur in both arteries and veins.

To date two types of anticoagulants, i.e. hepazins and vitamin K antagonists, are in clinical use to prevent thrombosis. Both act indirectly by reducing the activity of thrombin. Heparin mainly acts by accelerating the inactivation of thrombin by its physiological inhibitors like antithrombin III and heparin cofactor II. Heparin only acts when given parenterally. The vitamin K antagonists, of which the coumarin derivative warfarin is a well-known example, are orally active and act by inhibiting the production in functional form of a number of vitamin K dependent coagulation factors (II, VII, IX and X). Because of their mechanism of action these latter agents have a slow onset and reversal of action. Major clinical problems associated with the use of heparins and coumarins are bleeding and their small and unpredictable therapeutic safety margin.

There is a need therefore to develop improved coagulation inhibitors, which for instance inhibit thrombin or factor Xa directly.

SUMMARY OF THE INVENTION

Its is found that compounds which comprise the 3,8-diamino-8a-hydroxyimidazo[1,5-a]zpyridine-1(5H)-one unit of the invention are inhibitors of serine proteases, that require a basic amino acid residue (i.e. arginine, lysine) at the $P_1$ position of their substrates. These compounds are presumably capable of interacting at the primary specificity site $S_1$ of the protease. Selectivity in their mode of action is further determined by the substituent at the 8-amino group of the 3,8-diamino-8a-hydroxyimidazo[1,5-a]pyridine-1 (5H)-one unit. The substituent may be any group which is capable to interact with the $S_n \ldots S_2$ subsites, and preferably a peptidyl group that is homologous to the $P_n \ldots P_2$ subsites of the substrate of the pertinent enzyme or may be any derivative or mimic of the $P_n \ldots P_2$ substrate sites that binds to the putative $S_n \ldots S_2$ subsites of the active site of the enzyme.

DETAILED DESCRIPTION OF THE INVENTION

A preferred embodiment of the present invention relates to inhibitors of serine proteases, like thrombin and factor Xa, that are involved in the process of thrombosis and haemostasis. The inhibitors according to a preferred embodiment comprise the unit having formula I and a substituent at the 8-amino group that is a homologue, a derivative or a mimic of the $P_3$-$P_2$ subsites of the substrate of the pertinent serine protease. A variety of such $P_3$-$P_2$ derivatives are already known in the art, for example as described by Hauptmann and Markwardt (Seminars in Thrombosis and Hemostasis, 18, 200–217, 1992), Jakubowski et.al. (Annual Reports in Medicinal Chemistry, 27, 99–108, 1992) and Shuman et.al. (J. Med. Chem. 36, 314–319, 1993), which are incorporated herein by reference.

Preferred compounds according to the invention are the 3,8-diamino-8a-hydroximidazo[1,5a]pyridin-1[5a]-one derivatives of formula I wherein $R_1$, $R_2$, $R_3$ and $R_4$ are hydrogen.

In a more preferred embodiment the present invention relates to serine protease inhibitors having formula II,

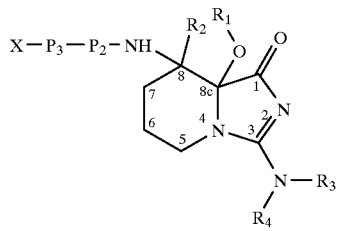

II wherein $R_1$, $R_2$, $R_3$ and $R_4$ are hydrogen; X is hydrogen, $R_7$, $R_7$—O—C(O)—, $R_7$—C(O)—, $R_7$—SO$_2$—, —(CHR$_8$)$_m$COOR$_8$, or an N-protecting group, wherein $R_7$ is (1–12C) alkyl or (2–12C)alkenyl, which groups may optionally be substituted with (3–8C)cycloalkyl, (1–6C)alkoxy, OH or halogen, or $R_7$ is (3–8C)cycloalkyl, (4–10C)heterocyclyl, (4–14C)aryl, (7–15C)aralkyl and (8–16C)aralkenyl, which groups may optionally be substituted with (1–6C)alkyl, (3–8C)cycloalkyl, (1–C)alkoxy, OH or halogen, and the aryl groups of which may optionally comprise a heteroatom; each group $R_8$ is independently hydrogen or has the same meaning as $R_7$; m is 1, 2 or 3; $P_3$ is a bond, an amino-acid of the formula —NH—CH[(CH$_2$)$_p$C(O)OH]—C(O)— or an ester derivative thereof and p being 0, 1, 2 or 3, —N(benzyl)—CH$_2$—CO—, D-Tiq, Atc, 3-Piq, 1-Piq or a D-amino acid having a hydrophobic side chain; $P_2$ is Pro or Pec, optionally substituted with (1–4C)alkyl, halogen, hydroxy or oxo, or an amino acid selected from Gly, Val, Hie, 2,4-MePro, 3,3-Dmp, Ilc, Thz, Hyp, 2,2-Dmt, 5,5-Dmt, Lac, Apy, Ac$_5$c, 1-Nal and 2-Nal, or $P_2$ is an amino acid of the formula —N[(3–8C)cycloalkyl]—CH$_2$—C(O)—, the ring of which may optionally be substituted with (1–6C) alkyl, halogen, hydroxy or oxo; or $P_2$ is a bond in which case $P_3$ is also a bond and X is $R_7$—SO$_2$—; or $P_2$ and $P_3$ together represent a dipeptide mimicking structure having formula III

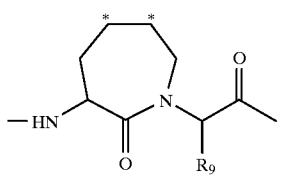

III which at the positions indicated with an asterisk may be fused with a benzene ring and wherein $R_9$ is hydrogen or lower alkyl.

The N-protecting group as defined in the definition of moiety X is any N-protecting group as commonly used in peptide chemistry for the protection of an α-amino group, like the tert-butyloxycarbonyl(Boc) group, the benzyloxycarbonyl (Z) group, the 9-fluorenyl-methyloxycarbonyl (Fmoc) group or the phthaloyl (Phth) group. Suitable N-protecting groups can further be found in T. W. Green and P. G. M. Wuts. Protective Groups in Organic Synthesis, Second Edition (Wiley, NY, 1991) and in The Peptides, Analysis, Synthesis, Biology, Vol. 3 E. Gross and J. Meienhofer, Eds., (Academic Press, New York, 1981).

The term (1–12C)alkyl means a branched or unbranched alkyl group having 1 to 12 carbon atoms, such as methyl, ethyl, t-butyl, isopentyl, heptyl, dodecyl, and the like. Preferred alkyl groups are (1–6C)alkyl groups, having 1–6 carbon atoms. Most preferred are (1–4C)alkyl groups, having 1–4 carbon atoms, such as methyl, ethyl, isopropyl, n-butyl and t-butyl.

A (2–12C)alkenyl group is a branched or unbranched unsaturated hydrocarbon group having 2 to 12 carbon atoms. Examples are ethenyl, propenyl, allyl, and the like.

The term (1–6C)alkoxy means an alkoxy group having 1–6 carbon atoms, the alkyl moiety of which having the meaning as previously defined.

The term (3–8C)cycloalkyl means a cycloalkyl group having 3–8 carbon atoms, being cyclopropyl, cyclobutyl, cyclopentyl, cyclohexyl, cycloheptyl or cyclo-octyl. Cyclopentyl and cycolhexyl are preferred cycloalkyl groups.

The term (4–10C)heterocyclyl means a substituted or unsubstituted cyclic hydrocarbon group, having 4 to 10 carbon atoms, also containing one or two heteroatoms selected from N, O, and S, like 3-methyl-1,2,3,4-tetrahydro-8-quinolinyl. Substituents on the heterocyclic group may be selected from groups such as (1–6C)alkoxy, hydroxy, halogen, nitro, amino, dialkylamino or lower alkyl. The term dialkylamino means a dialkylamino group wherein alkyd has the meaning of lower alkyl as previously defined. A (4–14C)aryl group is an aromatic moiety of 4 to 14 carbon atoms. The aryl group may further contain one or two hetero atoms and may be substituted, e.g. with (1–6C)alkyl, (3–8C) cycloalkyl, (1–6C)alkoxy, hydroxy, nitro, amino, dialkylamino or halogen. Examples of aryl groups are phenyl, dimethoxyphenyl, naphthyl, 4-biphenyl, iridazolyl, thienyl, benzthienyl, (iso)quinolyl, 3-methyl-8-quinolinyl, indanyl, indolyl and the like. Preferred aryl groups are phenyl and naphthyl.

(7–15C)aralkyl and (8–16C)aralkenyl groups are alkyl and alkenyl groups respectively, substituted by one or more aryl groups, the total number of carbon atoms being 7 to 15 and 8 to 16, respectively.

The term halogen means fluorine, chlorine, bromine or iodine. The term ester derivative means any appropriate ester derivative, preferably (1–4C)alkyl-esters, such as methyl-, ethyl- or t-butyl-esters.

The term hydrophobic side chain means a (1–12C)alkyl, optionally substituted with a (3–8C)cycloalkyl group or aromatic group (which may contain a heteroatom, e.g. nitrogen) such as cyclohexyl, cyclo-octyl, phenyl, pyridinyl, naphthyl, tetrahydronaphthyl, and the like, which hydrophobic side chain may optionally be substituted with substituents such as halogen, nitro, trifluoromethyl, lower alkyl (for instance methyl or ethyl), (1–6C)alkoxy (for instance methoxy), phenyloxy, benzyloxy, and the like. In the compounds according to formula III, the meaning of lower alkyl in the definition of $R_9$ is as previously defined.

Particularly preferred are serine protease inhibitors of formula II wherein $R_1$, $R_2$, $R_3$ and $R_4$ are hydrogen; X is hydrogen, lower alkyl, an acyl group, $R_7$—$SO_2$—, wherein $R_7$ is (4–10C)heterocyclyl, (6–14C)aryl, which aryl groups may contain a heteroatom, or X is an N-protecting group; $P_3$ is a bond in which case X is $R_7$—$SO_2$—, or $P_3$ is selected from D-Phe, D-Nle, D-Dpa, D-MePhe, D-1-Tiq, D-Cyk, D-Phg, D-Tic, D-Atc, D-2-Nal, D-2-Pal, D-Chg, and D-2-Nag; $P_2$ is selected from Pro, Pec, Gly, Val, Ile, 2,4-MePro, 3,3-Dmp, Ilc, Thz, Hyp, 2,2-Dmt, 5,5-Dmt, Lac, Apy, and $Ac_5c$; or $P_2$ is a bond in which case $P_3$ is also a bond and X is $R_7$—$SO_2$—; $P_2$ and $P_3$ together represent the dipeptide mimicking structure having formula III, the positions indicated with an asterisk being fused with benzene. The aromatic amino acid residues in the definition of $P_3$ in formula II in these preferred serine protease inhibitors, e.g. Phe, Dpa, Tiq, Phg, Nal, and Nag, may be substituted at the pertinent aromatic ring(s) by (1–6C)alkyl, (1–6C)alkoxy, halogen, hydroxy or nitro. Preferred phenylalanine (Phe) or phenylglycine (Phg) derivatives have a chloro or a nitro substituent at the para-positions of the phenyl group.

In a most preferred embodiment of the invention the serine protease inhibitor is in the form of the acetate.

The compounds according to the general formula II can be prepared by condensation of X-$P_3$-$P_2$-OH with a 3,8-diamino-8a-hydroxyimidazo[1,5a]pyridin-1(5H)-one derivative having formula IV

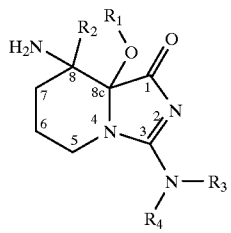

IV in which $R_1$, $R_2$, $R_3$, $R_4$, $P_2$, $P_3$ and X have the meanings as previously defined.

In those instances where X-$P_3$-$P_2$-OH represents a dipeptidyl group, or $R_7$-$SO_2$-$P_2$-OH or contains the dipeptide-mimicking structure of formula III, the condensation can be carried out by activation of the carboxylic acid function on the otherwise suitably protected structure, by methods commonly used for the condensation of peptide fragments such as by the azide method, mixed anhydride method, activated ester method or, preferably, by the carbodiimide method, especially with the addition of catalytic and racemization-suppressing compounds like N-hydroxysuccinimde and N-hydroxybenzotriazole. An overview of these condensation methods, which are common in peptide chemistry, is given in *The Peptides, Analysis, Synthesis, Biology*, Vol 3, ibid., which is included by reference.

In those instances where X represents $R_7$—$SO_2$ and $P_2$ and $P_3$ are a bond, the condensation can be carried out by using an activated sulfonylhalide derivative, such as $R_7$—$SO_2Cl$, wherein $R_7$ has the meaning as previously defined.

The compounds of formula IV can be prepared from 3-amino-6-guanidino-2-oxohexanoic acid derivatives of the general formula V

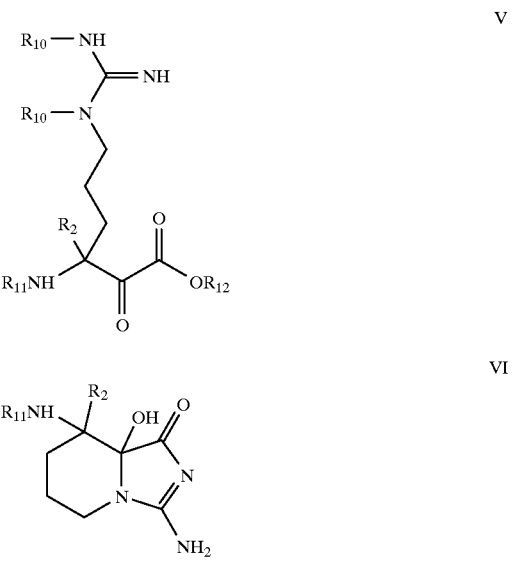

wherein $R_2$ has the meaning as defined for formula I, and wherein $R_{10}$ and $R_{11}$ represent a N-protecting group that is common in peptide chemistry and $R_{12}$ represents lower alkyl, as previously defined, by removal of the guanidino protecting groups $R_{10}$, after which the compound VI obtained, wherein $R_2$ and $R_{11}$ have the meanings as defined for formula V, is optionally alkylated, acylated or converted to the 8-[(amino)methylene]-amino derivative of compound VI by methods known in the art, after which $R_{11}$ is removed.

The 3-amino-6-guanidino-2-oxohexanoic acid derivatives of the general formula V can be prepared by introducing protecting groups at the α-amino group and at the guanidino group of the amino acid arginine or of a 2-alkyl substituted arginine, and subsequent conversion of the carboxylic acid function into an α-keto ester function by methods known in the art.

The compounds of the invention can be used in the manufacture of medicaments for the treatment and prophylaxis of thrombin mediated and thrombin-associated diseases. Such diseases include pulmonary embolism, thrombophlebitis, arterial occlusion from thrombosis or embolism, arterial reocclusion during or after angioplasty or thrombolysis, deep vein thrombosis, restenosis following arterial injury or invasive cardiological procedures, postoperative venous thrombosis or embolism, acute or chronic atherosclerosis, stroke, and myocardial infarction. Such diseases occur with, for example, certain types of cancer and metastasis, and neurodegenerative diseases.

The compounds of the invention can also be used as anticoagulants in vitro.

The novel compounds of formula I or II, which can occur in the form of a free base, may be isolated from the reaction mixture in the form of a pharmaceutically acceptable salt. The pharmaceutically acceptable salts may also be obtained by treating the free base of formula I or II with an organic acid, such as acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention may possess one or more chiral carbon atoms, and may therefore be obtained as a pure enantiomer, or as a mixture of enantiomers, or as a mixture containing diastereoisomers. Methods for obtaining the pure enantiomers are well known in the art, e.g. crystallization of salts which are obtained from optically active acids and the racemic mixture, or chromatography using chiral columns.

The compounds of the invention may be administered enterally or parenterally, and for humans preferably in a daily dosage of 0.001–10 mg per kg body weight. Mixed with pharmaceutically suitable auxiliaries, e.g. as described in the standard reference, Gennaro et.al., Remington's Pharmaceutical Sciences (18th ed., Mack Publishing Company, 1990, see especially part 8: Pharmaceutical Preparations and their Manufacture), the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

For making dosage units, e.g. tablets, the use of conventional additives such as fillers, colorants, polymeric binders and the like is contemplated. In general any pharmaceutical acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

The following abbreviations of the amino acids have been used throughout this specification and in the claims:
Aic=2-aminoindan-2-carboxylic acid
Ac₅c=aminocyclopentane-2-carboxylic acid
Apy=aminopyrrolidone
Arg=arginine
Atc=2-ainotetralin-2-carboxylic acid
Cha=cyclohexylalanine
Chg=cyclohexylglycine
Cyk=cyclooctylalanine
3,3-Dmp=3,3-dimethylproline
2,2-Dmt=2,2-dimethylthiazolidine-4-carboxylic acid
5,5-Dmt=5,5-dimethylthiazolidine-4-carboxylic acid
Dpa=3,3-diphenylalanine
Hyp=4-hydroxyproline
Ilc=(S)-indoline-2-carboxylic acid
Lac=3-amino-2-oxo-1-piperidine ('δ-lactam')
MePhe=α-methylphenylalanine
2-Nag=2-naphthylglycine
1-Nal=1-naphthylalanine
2-Nal=2-naphthylalanine
Nle=norleucine
2-Pal=2-pyridylalanine
Pec=pipecolic acid
Phg=phenylglycine
1-Piq=1-carboxyperhydroisoquinoline
3-Piq=3-carboxyperhydroisoquinoline
Pro=proline
Thz=thiazolidine-4-carboxylic acid
Tic=1,2,3,4-tetrahydroisoquinoline-3-carboxylic acid
1-Tiq=1-carboxy-1,2,3,4-tetrahydroisoquinoline
Other abbreviations used are:
Ac=acetyl Pmc=2,2,5,7,8-pentamethylchroman-6-sulphonyl All peptide sequences mentioned in the application are written according to the generally accepted convention wherein the N-terminal amino acid is on the left and the C-terminal amino acid is on the right. If no configuration of the amino acid has been stated, all amino acids, both the naturally occurring and the "non-protein" amino acids, referred to in this application are in the L-form.

Ascending thin layer chromatography (TLC) was carried out using precoated silica plates (Merck, $F_{254}$) in the following solvent systems:
System A: dichloromethane-ethyl acetate=9:1 (v/v)
System B: n-butanol-pyridine-acetic acid-water=10:1:1:2 (v/v/v/v)
System C: ethyl acetate-pyridine-acetic acid-water= 63:20:6:11 (v/v/v/v)
System D: n-butanol-pyridine-acetic acid-water=6:1:1:2 (v/v/v/v)
System E: toluene:ethanol=8:2 (v/v)
System F: ethyl acetate-pyridine-acetic acid-water= 63:10:3:5.5 (v/v/v/v)
System G: dichioromethane:ethyl acetate=95:5 (v/v)
System H: ethyl acetate-pyridine-acetic acid-water=6:2:2:1 (v/v/v/v)

EXAMPLE 1

(Scheme I)

3,8-diamino-6,7,8,8a-tetrahydro-8a-hydroxyimidazo[1, 5a]pyridin-1(5H)-one (6)

A: $N^α,N^δ$,N-tri-benzyloxycarbonyl-L-Arginine methyl ester (Z-Arg($Z_2$)-OMe; 1).

$N^α,N^δ$,N-tri-benzyloxycarbonyl-L-Arginine (40 g), prepared as described (Jetten et.al. Tetrahedron Lett. 1991, 32, 6025–6028), was dissolved in a mixture of dichloromethane (1080 ml) and methanol (120 ml).

2-(1H-benzotriazol-1-yl)-1,1,3,3-tetramethyluronium tetrafluoroborate (TBTU; 22.4 g) was added to the solution, whereupon triethylamine was added to the solution until an apparent pH of 8. The mixture was stirred at room temperature for 1 hour, after which the solution was successively washed with water, a sodiumbicarbonate solution and water, dried and evaporated to give a solid residue, which was crystallized from methanol. Yield: 35 g. $R_f$ 0.60 (system G).

B: $N^α$, $N^δ$, N-tri-benzyloxycarbonyl-L-Arginal (Z-Arg($Z_2$)-H; 2)

A solution of diisobutylaluminumhydride in hexane (180 ml; 1 M) was added dropwise at −78° C. to a stirred solution of Z-Arg($Z_2$)-OMe (90 g) in dry dichloromethane (700 ml). The mixture was stirred for 1 hour at −78° C., after which a 20% (v/v) solution of concentrated hydrochloric acid in ethanol was added until pH 2. The mixture was extracted with dichloromethane. The extracts were washed with water, a sodium-bicarbonate solution, and water, dried (sodium sulfate) and evaporated to give a crude product (25 g), which was processed without further purification. $R_f$ 0.48 (system A).

C: 2-acetoxy-3-(benzyloxycarbonylamino)-6-(dibenzyloxy-carbonyl-guanidino)hexanenitrile (3)

A solution of sodium cyanide (28 g) and triethylbenzylammoniumchloride (35 g) in water (700 ml) and acetic anhydride (14 ml) were simultaneously added with stirring to a precooled solution of Z-Arg($Z_2$)-H (30 g) in dichloromethane (700 ml). The mixture was stirred for 30 minutes at 0–5° C. The organic layer was separated and subsequently washed with water and aqueous brine, dried (sodium sulfate)

and evaporated to give a residue, which was chromatographed on silica. Elution with dichloromethane/ethyl acetate (95:5, v/v) gave a solid product (17 g). $R_f$ 0.76 (system A)

D: 3-(benzyloxycarbonylamino)-6-(dibenzyloxycarbonyl guanidino)-2-hydroxyhexanoic acid methylester (4)

2-acetoxy-3-benzyloxycarlbonylamino)-6-(dibenzyloxycarbonyl-guanidino)hexanenitrile (6.0 g) was dissolved in a mixture of diethylether and methanol (3:1 v/v; 140 ml). At −78° C. hydrogen chloride gas was passed through the solution until a 3 M solution was obtained. The mixture was stirred for 16 hours at 5° C., whereupon the mixture was extracted with dichloromethane. The combined extracts were washed with water, a sodiumbicarbonate solution and water, dried (sodium sulfate) and evaporated to give a gum (6.1 g). $R_f$ 0.48 (system A).

E: 3-(benzyloxycarbonylamino)-6-(dibenzyloxycarbonyl guanidino)-2-oxo-hexanoic acid methylester (5)

Chromic acid (1.3 ml of a 8N solution in aqueous sulfuric acid) was slowly added to a precooled solution of 3-(benzyloxycarbonylamino)-6-(dibenzyloxycarbonyl guanidino)-2-hydroxyhexanoic acid methylester (1.3 g) in acetone (130 ml). The mixture was stirred for 1 hour at 0° C. and then poured into ice water. The precipitate was filtered off, washed with water and dried in vacuo to give a white solid (1.15 g). $R_f$ 0.80 (system A).

F: 3,8-diamino-6,7,8,8a-tetrahydro-8a-hydroxyimidazo [1,5a]pyridin-1(5H)-one (6)

Hydrochloric acid (1.04 ml of a 1M aqueous solution) and palladium on activated carbon (Pd/C 10%; 64 mg) were added to a solution of 3-(benzyloxycarbonylamino)-6-(dibenzyloxycarbonyl guanidino)-2-oxo-hexanoic acid methylester (644 mg) in dimethylformamide (20 ml). Hydrogen gas was passed through the solution until completion of the reaction as monitored by thin layer chromatography. The reaction mixture was filtered to remove the catalyst. The filtrate was evaporated in vacuo to give a oil (320 mg). $R_f$ 0.50 (system B).

EXAMPLE 2

(Scheme I)

$N^8$(D-phenylalanyl-prolyl)-3,8-diamino-6,7,8,8a-tetrahydro-8a-hydroxyimidazo[1,5a]pyridin-1(5H)-one (8)

1-Hydroxy-benzotriazole (233 mg) and dicyclohexylcarbodiimnde (261 mg) were successively added to a solution of Boc-D-Phe-Pro-OH (0.41 g) in dimethylformamide (10 ml), keeping the temperature at 0–5° C. The reaction mixture was stirred for 15 minutes, after which a solution of 3,8-diamino-6,7,8,8a-tetrahydro-8a-hydroxyimidazo [1,5a] pyridin-1(5H)-one (192 mg) in dimethylformamide (10 ml), the pH of which had previously been adjusted to 7 by addition of triethylamine, was added. The solution was stirred for 16 hours at room temperature, after which the precipitated dicyclohexylurea was filtered off. The filtrate was evaporated to a small volume. n-Butanol was added, whereupon the solution was washed with a sodiumbicarbonate solution and water, dried (sodium sulfate) and evaporated to give the $N^\alpha$-Boc-protected compound 7 (0.89 g). $R_f$ 0.50 (system C).

The crude product was dissolved at 0° C. in 90% aqueous trifluoroacetic acid (15 ml), also containing anisole (0.43 ml). The mixture was stirred for 2 hours at room temperature and subsequently evaporated in vacuo. The residue was dissolved in tert-butanol-water (1:1 v/v) and Dowex-2 (X-8, acetate form) was added in portions until the pH of the solution was raised to 5–6. The ion exchange resin was filtered off, after which the filtrate was lyophilized. The product was chromatographed on silica. Elution with n-butanol-pyridine-acetic acid-water (8:1:1:2 v/v) gave the title compound 8 (120 mg). $R_f$ 0.70 (system D)). NMR specral data were in agreement with the structure having the 8S,8aR-configuration.

Scheme I

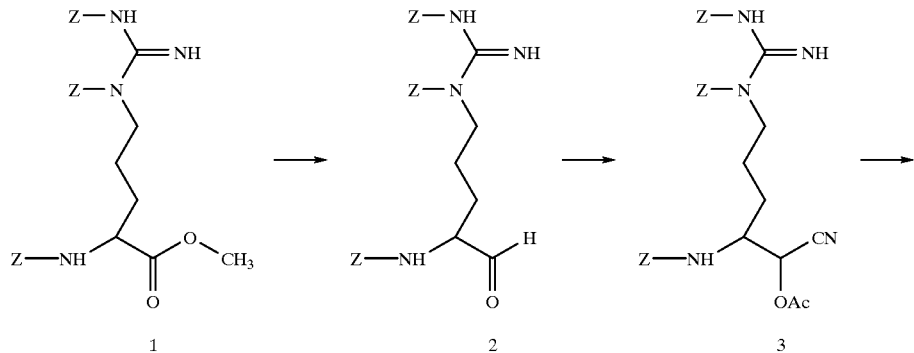

-continued

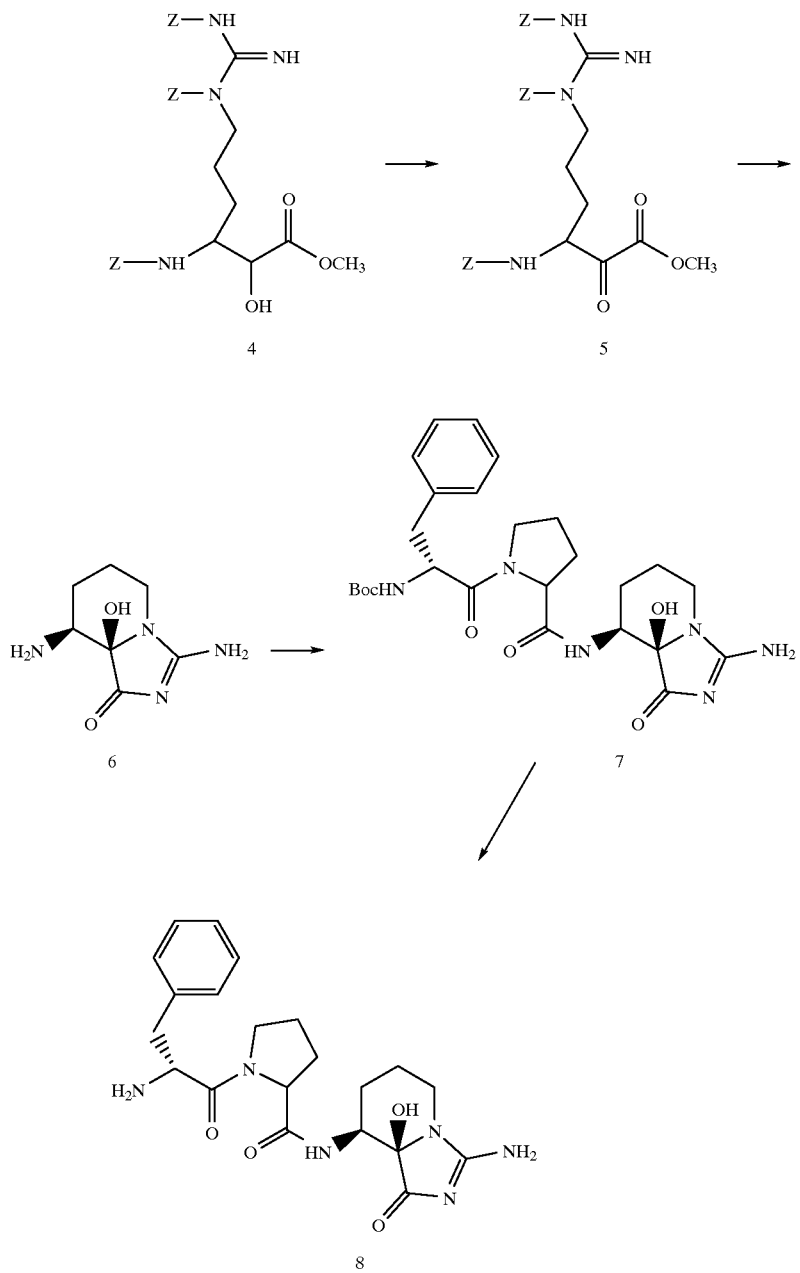

EXAMPLE 3

N$^s$(N$^\alpha$(methyl)-D-phenylalanyl-prolyl)-3,8-diamino-6,7,8,8a-tetrahydro-8a-hydroxyimidazo[1,5a]pyridin-1(5H)-one A: Z-N(Me)-D-Phe-OH Carbobenzoxychloride (6.4 mmoles) was added to a solution of H-N(Me)-D-Phe-OH (4.0 mmoles) and sodium hydroxide (4.0 mmoles) in dioxane-water (1;1, v/v). The solution was stirred for 24 hours, while keeping the pH at 12 by addition of sodium hydroxide (4N solution in water). The reaction mixture was extracted with diethylether to remove the excess of carbobenzoxychloride. Aqueous hydrochloric acid was added to the solution until pH 2. The precipitated product was extracted with ethyl acetate. The organic layer was washed with brine, dried (sodium sulfate) and evaporated in vacuo to give a syrup (76%). R$_f$0.45 (system E).

B: Z-N(Me)-D-Phe-Pro-OMe

Z-N(Me)-D-Phe-OH (3 mmoles), H-Pro-OMe.HCl (3 mmoles) and N-hydroxybenzotriazole (6 mmoles) were dissolved in dimethylformamide (20 ml). 4-Ethylmorpholine was added to the solution until pH 6.5, after which the solution was cooled to 0° C. A solution of dicyclohexylcarbodiimide (3.3 mmoles) in dimethylformamide (5 ml) was slowly added to the cold solution. The mixture was stirred for 1 hour at 0° C. and then for 16 hours at room temperature. Precipitated dicyclohexylurea was filtered off and the filtrate was evaporated in vacuo to give a syrup, which was dissolved in ethyl acetate. The solution was subsequently washed with a sodium bicarbonate solution, a sodiumbisulfate solution and brine, dried (sodium sulfate) and evaporated in vacuo to give a foam (96%). $R_f$ 0.47 (system E).

C: Z-N(Me)-D-Phe-Pro-OH

Sodium hydroxide (6 mmoles; 4N aqueous solution) was added to a solution of Z-N(Me)-D-Phe-Pro-OMe (3 mmoles) in dioxane-water (1:1, v/v) while stirring. The solution was kept at room temperature for 16 hours. The solution was diluted with water and extracted with diethyether. Hydrochloric acid was added to the aqueous solution until pH 2. The precipitated product was extracted with ethyl acetate. The combined extracts were washed with brine, dried (sodium sulfate) and evaporated to give a foam (0.94 g; 77%). $R_f$ 0.22 (system E).

D: The title compound was prepared by coupling 3,8-diamino-6,7,8,8a-tetrahydro-8a-hydroxyimidazo [1,5a] pyridin-1(5H)-one and Z-N(Me)-D-Phe-Pro-OH using the coupling method as described in Example 2, followed by removal of the N-benzyloxycarbonyl protecting group by catalytic dehydrogenation. $R_f$ 0.60 (system C)

EXAMPLE 4

$N^8$(D-diphenylalanyl-prolyl)-3,8-diamino-6,7,8,8a-tetrahydro-8a-hydroxyimidazo[1,5a]pyridin-1(5H)-one A: Z-D-Dpa-OH A solution of N-(benzyloxycarbonyloxy)succinimide (Z-ONSu; 2.0 mmoles) in dioxane (15 ml) was slowly added while stirring to a solution of D-diphenylalanine (H-D-Dpa-OH; 2.0 mmoles) in 10% (w/v) aqueous solution of sodiumbicarbonate. The mixture was stirred for 2 days, after which the mixture was washed with diethylether. The aqueous solution was acidified to pH 1–2 by addition of hydrochloric acid. The precipitated product was extracted with ethyl acetate. The combined extracts were washed with brine, dried (sodium sulfate) and evaporated to give an oil (0.74 g; 100%). $R_f$ 0.77 (system E).

B: Z-D-Dpa-Pro-OtBu

Z-D-Dpa-OH (2.0 mmoles), H-Pro-OtBu.HCl (2.0 mmoles) and N-hydroxybenzotriazole (4 moles) were dissolved in dimethylformamide (15 ml). 4-Ethylmorpholine was added to the stirred solution until pH 6.5, after which the solution was cooled to 0° C. A solution of dicyclohexylcarbodiimide (2.2 mmoles) in dimethylformamide (4 ml) was slowly added to the cold reaction mixture, which was then stirred for 1 hour at 0° C. and a further 16 hours at room temperature. Precipitated dicyclohexylurea was filtered off and the filtrate was evaporated in vacuo to give a syrup, which was dissolved in ethyl acetate. The solution was subsequently washed with a sodium bicarbonate solution, a sodiumnbisulfate solution and brine, dried (sodium sulfate) and evaporated in vacuo to give a oil (0.88 g; 83%). $R_f$ 0.69 (system E).

C: Z-D-Dpa-Pro-OH

Z-D-Dpa-Pro-OtBu (1.67 mmoles) was dissolved at 0° C. in 90% aqueous trifluoroacetic acid (15 ml), also containing anisole (0.43 ml). The mixture was stirred for 30 minutes at room temperature and subsequently evaporated in vacuo. The residue was triturated with diethyl ether to give a solid (0.33 g; 42%).

$R_f$ 0.53 (system E). FAB-MS: mm 472

D: The title compound was prepared by coupling 3,8-diamino-6,7,8,8a-tetrahydro-8a-hydroxyimidazo[1,5a] pyridin-1(5H)-one and Z-D-Dpa-Pro-OH using the coupling method as described in Example 2, followed by removal of the $N^\alpha$-benzyloxycarbonyl protecting group by catalytic dehydrogenation. $R_f$ 0.40 (system C).

EXAMPLE 5

$N^8$(H-D-Phe-Ilc)-3,8-diamino-6,7,8,8a-tethydro-8a-hydroxyimidazo[1,5a]pyridin-1(5H)-one A: Z-D-Phe-Ilc-OH 4-Ethylmorpholine (1 mmole) was added to a solution of (S)-indoline-2-carboxylic acid (1 mmole; 163 mg) and the N-carboxyanhydride of Z-D-Phe-OH (4 mmoles; 1.3 g) in dry tetrahydrofuran (10 ml). The mixture was stirred at room temperature for 16 hours after which the solvent was evaporated in vacuo. The crude product was purified by counter current distribution in the solvent system dichloromethane-methanol-toluene-water (5:8:5:3; v/v/v/v) to give Z-D-Phe-Ilc-OH in quantitative yield (0.45 g). $R_f$ 0.60 (system F). FAB-MS: mm 444.

B: $N^8$(Z-Phe-Ilc)-3,8-diamino-6,7,8,8a-tetrahydro-8a-hydroxyimidazo[1,5a]pyridin-1(5H)-one 4-Ethylmorpholine (0.67 mmoles) was added to a dimethylformamide (12 ml) solution of Z-D-Phe-Ilc-OH (0.67 mmoles; 300 mg) and 3,8-diamino-6,7,8,8a-tetrahydro-8a-hydroxyimidazo [1,5a]pyridin-1(5H)-one (0.71 mmoles; 320 mg). N-hydroxybenzotriazole (1.1 mmoles; 150 mg) and dicyclohexylcarbodiimide (0.71 mmoles; 147 mg) were successively added to the solution, while keeping the temperature at 0–2° C. The mixture was stirred at this temperature for 1 hour, and a further 16 hours at room temperature. Dicyclohexylurea was filtered off, after which the filtrate was evaporated in vacuo. The residue was dissolved in n-butanol. The solution was washed with a sodium bicarbonate solution and brine, dried (sodium sulfate) and evaporated in vacuo to give a foam (322 mg; 70%). $R_f$ 0.37 (system C).

C: Palladium on activated coal (Pd/C 10%; 30 mg) was added to a solution of the product of Example 5 (0.43 mmoles; 300 mg) in methanol (10 ml). Hydrogen gas was passed through the solution, while stirring, for 16 hours. The catalyst was removed by filtration, after which the filtrate was evaporated in vacuo. The residue was chromatographed on aluminumoxide (Lichroprep AloxT; 25–30 μm). Elution with ethyl acetate-pyridine-acetic acid-water (63:20:6:11; v/v/v/v) gave the title compound (135 mg; 45%). $R_f$ 0.35 (system C).

EXAMPLE 6

In a similar manner as described in Examples 1–5 were prepared:

$N^8$(H-D-MePhe-Pro)-3,8-diamino-6,7,8,8a-tetrahydro-8a-hydroxyimidazo[1,5a]pyridin-1(5H)-one $N^8$(H-D-1-Tiq-Pro)-3,8-diamino-6,7,8,8a-tetrahydro-8a-hydroxyimidazo[1,5a]pyridin-1(5H)-one $N^8$(H-D-Nle-Pro)-3,8-diamino-6,7,8,8a-tetrahydro-8a-hydroxyimidazo[1,5a]pyridin-1(5H)-one $N^8$(Pmc-Gly)-3,8-diamino-6,7,8,8a-tetrahydro-8a-hydroxyimidazo-[1,5a]pyridin-1(5H)-one $N^8$(Phth-Gly)-3,8-diamino-6,7,8,8a-tetrahydro-8a-hydroxyimidazo[1,5a]pyridin-1(5H)-one $N^8$(H-D-Atc-Pro)-3,8-diamino-6,7,8,8a-tetrahydro-8a-hydroxyimidazo[1,5a]pyridin-1(5H)-one $N^8$(Ac-D-Phe-Pro)-3,8-diamino-6,7,8,8a-tetrahydro-8a-hydroxyimidazo[1,5a]-pyridin-1(5H)-one $N^8$(H-D-2-Nag-Pro)-3,8-diamino-6,7,8,8a-tetrahydro-8a-hydroxyimidazo[1,5a]pyridin-1(5H)-one $N^8$(H-D-Phe-3,3-Dmp)-3,8-diamino-6,7,8,8a-tetrahydro-8a-hydroxyimidazo[1,5a]pyridin-1(5H)-one $N^8$(H-D-Phe-2,4-MePro)-3,8-diamino-6,7,8,8a-tetrahydro-8a-hydroxyimidazo[1,5a]pyridin-1(5H)-one $N^8$(H-D-Phe-2,2-Dmt)-3,8-diamino-6,7,8,8a-tetrahydro-8a-hydroxyimidazo[1,5a]pyridin-1(5H)-one $N^8$(H-D-Phe-5,5-Dmt)-3,8-diamino-6,7,8,8a-tetrahydro-8a-hydroxyimidazo[1,5a]pyridin-1(5H)-one $N^8$(H-D-Phe-Thz)-3,8-diamino-6,7,8,8a-tetrahydro-8a-hydroxyimidazo[1,5a]pyridin-1(5H)-one $N^8$(H-D-Phe-Hyp)-3,8-diamino-6,7,8,8a-tetrahydro-8a-hydroxyimidazo[1,5a]pyridin-1(5H)-one

EXAMPLE 7

$N^8$[2-(S)[4(R)-(1,3-Dihydro-1,3-dioxo-2H-isoindol-2-yl)-1,3,4,5-tetrahydro-3-oxo-2H-2-benzazepin-2-yl]1-oxo-propyl]-3,8-diamino-6,7,8,8a-tetrahydro-8a-hydroxyimidazo[1,5a]pyridin-1(5H)-one A: N-Phthaloyl-D-phenylalanyl-L-alanine methyl ester To a solution of L-alanine methyl ester hydrochloride (1.15 g, 8.3 mmol) in dichloromethane (20 ml) was added triethylamine (1.15 ml, 8.3 mmol), followed by N-phthaloyl-D-phenylalanine (2.44 g, 8.3 mmol) and N-hydroxybenzotriazole (1.27 g, 9.1 mmol). the mixture was stirred until a clear yellow solution was formed. The solution was cooled to 0° C., and 1-[3-(dimethylamino)-propyl-3-ethyl] carbodiimide (1.74 g, 9.1 mmol) was added. After stirring at room temperature for 64 h, the solution was diluted with dichloromethane (50 ml). Aqueous hydrochloric acid (1N; 50 ml) was added and the resulting suspension was filtered. The layers were separated, and the organic phase was washed with aqueous hydrochloric acid (1N; 15 ml), saturated aqueous sodium bicarbonate (50 ml), water (50 ml), and brine (50 ml), successively. The organic extract was dried (sodium sulfate) and evaporated to give 2.50 g (80%) of crystalline material. An analytical sample was crystallized from ethyl acetate/heptane, m.p. 118–120° C.

B: N-Phthaloyl-D-phenylalanyl-L-alanine

To a solution of N-phthaloyl-D-phenylalanyl-L-alanine methyl ester (1.46 g, 3.8 mmol) in acetone (20 ml) was added, water (11 ml) and concentrated HCl (6 ml). The mixture was refluxed for 3.5 h. After cooling to room temperature, 0.80 g (2.1 mmol) of the title compound was isolated by filtration. The mother liquor was concentrated to remove the acetone, and the aqueous solution was extracted with ethyl acetate (3×20 ml). The organic layers were extracted with saturated aqueous sodium bicarbonate (3×25 ml). The combined aqueous extracts were washed with ethyl acetate (25 ml), and adjusted to pH 1 with concentrated hydrochloric acid. Ethyl acetate was added (50 ml), the layers were separated, and the aqueous was extracted with ethyl acetate (2×25 ml). The combined ethyl acetate extracts were washed with brine (2×50 ml), dried (sodium sulfate) and evaporated to give 0.50 g of the title acid. Total yield 1.30 g (3.6 mmol, 92%). Crystals from methanol, m.p. 241–242° C.

C: 3-[2(R)-(1,3-Dihydro-1,3-dioxo-2H-isoindol-2-yl)-4(S)-methyl-1-oxo-3-phenylpropyl]-5-oxazolidinone To a solution of N-phthaloyl-D-phenylalanyl-L-alanine (0.50 g, 1.4 mmol) in dry dichloromethane was added, excess paraformaldehyde (0.50 g) and mol. sieve 4 Å (2.5 g). The suspension was stirred for 30 min at room temperature. Triflic acid (120 μl, 1.4 mmol) was added and stirring was continued for 24 h. The solution was filtered, washed with saturated aqueous sodium bicarbonate (2×25 ml) and brine (25 ml). The organic phase was dried (sodium sulfate) and evaporated till dryness. The residue was purified by column chromatography (silica, ethyl acetate/heptane 1:2) to give 400 mg (1.1 mmol, 80%) of the title compound, Rf (ethyl acetate/heptane 2:1) 0.45.

D: 4(R)-(1,3-Dihydro-1,3-dioxo-2H-isoindol-2-yl)α(S)-methyl-1,3,4,5-tetrahydro-3-oxo-2H-2-benzazepin-2-acetic acid.

The oxazolidinone (250 mg, 0.7 mmol), obtained as described above, was dissolved in dry dichloromethane (1 ml) and added to triflic acid (1 ml). The mixture was vigorously stirred for 2h. After dilution of the reaction mixture with dichloromethane (10 ml), water (15 ml) was added cautiously with continued vigorous stirring. The layers were separated and the aqueous phase was extracted with dichloromethane (2×10 ml). The combined organic layers were washed with brine (25 ml), dried (sodium sulfate), and evaporated. The residue was crystallized from ethanol/diethyl ether to give 150 mg (0.4 mmol, 60%) of the title compound, m.p. 209–210° C.

E: $N^8$[2-(S)[4(R)-(1,3-Dihydro-1,3-dioxo-2H-isoindol-2-yl)-1,3,4,5-tetrahydro-3-oxo-2H-2-benzazepin-2-yl]1-oxo-propyl]-3,8-diamino-6,7,8,8a-tetrahydro-8a-hydroxyimidazo[1,5a]pyridin-1(5H)-one To a solution of 3,8-diamino-6,7,8,8a-tetrahydro-8a-hydroxyimidazo [1,5a]pyridin-1(5H)-one.2HCl (90 mg, 57% pure, 0.19 mmol) in dry dimmethylformamide (15 ml), was added the acid described under D (75 mg, 0.19 mmol). The pH was adjusted to 7.4 with 4-ethylmorpholine, and N-hydroxybenzotriazole (45 mg, 0.3 mmol) was added. After cooling to 0° C., dicyclohexyl carbodiimide (42 mg, 0.2 mmol) was added, and the resulting solution was stirred for 3 h at 0° C. and a further 33 h at room temperature. The solution was partly evaporated, and a few drops of water were added. The solution was stirred for 30 min., filtered and evaporated till dryness. Purification by column chromatography (aluminium oxide; elution with ethyl acetate: pyridine: acetic acid: water=6/2/2/1, v/v/v/v) gave 75 mg of the title compound. $R_f$ 0.65 (system H)

EXAMPLE 8

3-[[(dimethylamino)methylene]amino]-$N^8$(2-naphthylsulfonyl)-8-amino-6,7,8,8a-tetrahydro-8a-hydroxyimidazo-[1,5a]pyridin-1(5H)-one Triethylamine was added to a solution of 3,8-diamino-6,7,8,8a-tetrahydro-8a-hydroxyimidazo[1,5a]pyridin-1(5H)-one (100 mg) in dimethylformamide (10 ml) until an apparent pH of 8. 2-Naphthylsulfonylchloride (135.5 mg) and an equimolar amount of triethylamine were successively added to the solution while stirring. The mixture was stirred for 16 hours at room temperature, after which the volatiles were removed. The residue was purified by column chromatography (silica, ethyl acetate-pyridine-acetic acid-water= 5:2:2:1; v/v/v/v) to give the title compound (12.6 mg). $R_f$ 0.45 (system C).

EXAMPLE 9

$N^8$(2-naphthylsulfonyl)-3,8-diamino-6,7,8,8a-tetrahydro-8a-hydroxyimidazo[1,5a]pyridin-1(5H)-one Triethylamine was added to a solution of 3,8-diamino-6,7,8,8a-tetrahydro-8a-hydroxyimidazo[1,5a]pyridin-1(5H)-one (257 mg) in dimethylformamide (10 ml) until an apparent pH of 8. 2-Naphthylsulfonylchloride (227 mg) and an equimolar amount of triethylamine were successively added to the solution while stirring. The mixture was stirred for 16 hours at room temperature, after which the volatiles were removed. The residue was purified by column chromatography (silica, ethyl acetate-pyridine-acetic acid-water= 5:2:2:1; v/v/v/v) to give the title compound (26 mg). $R_f$ 0.30 (system C).

EXAMPLE 10

N^8[N^α(2-naphthylsulfonyl)glycyl]-3,8-diamino-6,7,8,8a-tetrahydro-8a-hydroxyimidazo[1,5a]pyridin-1(5H)-one N^α(2-naphthylsulfonyl)glycine (2-Nas-Gly-OH; 1.0 mmole)—prepared by condensation of 2-naphthylsulfonylchloride and methylglycinate, followed by saponification of the methyl ester in aqueous sodium hydroxide—, 3,8-diamino-6,7,8,8a-tetrahydro-8a-hydroxyimidazo [1,5a]pyridin-1(5H)-one.2HCl (1.0 mmole) and N-hydroxybenzotriazole (2.0 mmoles) were dissolved in dimethylformamide (15 ml). The pH of the solution was adjusted to 6.5 by the addition of 4-ethylmorpholine, whereupon the solution was cooled to 0° C. and dicyclohexylcarbodiimide (1.1 mmoles) was added. The mixture was stirred for 1 hour at 0° C. and a further 17 hours at room temperature. The precipitated dicyclohexylurea was filtered off and the filtrate was evaporated to leave a residue, which was dissolved in butanol. The organic solution was washed with 5% (w/v) sodium bicarbonate solution and with brine, whereupon the butanol was removed in vacuo. The crude product was subsequently purified by chromatography on aluminiumoxide (Alox T; 25–40 μm) to give the title compound (70 mg). $R_f$ 0.40 (system H).

We claim:

1. An imidazole[1,5a]pyridine derived serine protease inhibitor of formula I

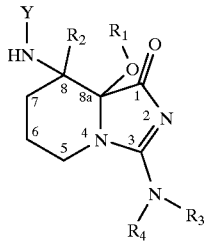

(I)

wherein $R_1$ is hydrogen, lower alkyl or an acyl group;

$R_2$ is hydrogen or lower alkyl;

$R_3$ and $R_4$ are independently hydrogen, lower alkyl or together form =CH—NR_5R_6, wherein $R_5$ and $R_6$ are lower alkyl;

Y is a group capable of interacting with the $S_n \ldots S_2$ subsites of the active site of a serine protease;

or a pharmaceutically acceptable salt thereof.

2. The serine protease inhibitor of claim 1, wherein $R_1$, $R_2$, $R_3$, and $R_4$ are hydrogen.

3. The serine protease inhibitor of claim 1 wherein the inhibitor is in the form of the acetate.

4. An imidazole[1,5a]pyridine derived serine proteases inhibitor of formula I

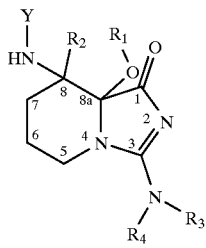

(I)

wherein $R_1$ is hydrogen, lower alkyl or an acyl group;

$R_2$ is hydrogen or lower alkyl;

$R_3$ and $R_4$ are independently hydrogen, lower alkyl or together form =CH—NR_5R_6, wherein $R_5$ and $R_6$ are lower alkyl;

Y is a peptidyl group that is homologous to the $P_n \ldots P_2$ subsites of the substrate of a serine protease;

or a pharmaceutically acceptable salt thereof.

5. A serine protease inhibitor of formula II

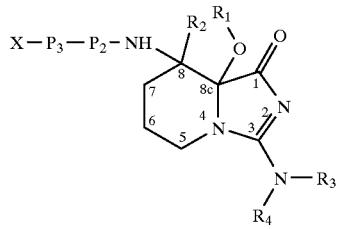

II wherein $R_1$, $R_2$, $R_3$ and $R_4$ are hydrogen;

X is selected from the group consisting of hydrogen, $R_7$, $R_7$—O—C(O)—, $R_7$—C(O)—, $R_7$—SO_2—, —(CHR_8)_mCOOR_8, and an N-protecting group, wherein $R_7$ is $(C_{1-12})$alkyl or $(C_{2-12})$alkenyl, which are unsubstituted or substituted with $(C_{3-8})$cycloalkyl, $(C_{1-6})$alkoxy, OH or halogen, or $R_7$ is $(C_{3-8})$cycloalkyl, $(C_{4-10})$ heterocycle, $(C_{4-14})$aryl, $(C_{7-15})$aralkyl or $(C_{8-16})$aralkenyl, which are unsubstituted or substituted with $(C_{1-6})$alkyl, $(C_{3-8})$cycloalkyl, $(C_{1-6})$alkoxy, OH or halogen, and wherein the aryl groups may contain a heteroatom;

each group $R_8$ is independently hydrogen or has the same meaning as $R_7$;

m is 1, 2 or 3;

$P_3$ is a bond, an amino acid of the formula —NH—CH[(CH_2)_pC(O)OH]—C(O)—, or an ester derivative thereof, and p is 0, 1, 2 or 3, —N(benzyl)—CH_2—CO—, D-Tiq, Atc, 3-Piq, 1-Piq or a D-amino acid having a hydrophobic side chain;

$P_2$ is Pro or Pec, which is unsubstituted or substituted with $(C_{1-4})$alkyl, halogen, hydroxy or oxo, or an amino acid selected from Gly, Val, Ile, 2,4-MePro, 3,3-Dmp, Ilc, Thz, Hyp, 2,2-Dmt, 5,5-Dmt, Lac, Apy, Ac_5c, 1-Nai and 2-Nal, or $P_2$ is an amino acid of the formula —N[(C_{3-8}) cycloalkyl]—CH_2—C(O)—, wherein the cycloalkyl is unsubstituted or substituted with $(C_{1-6})$ alkyl, halogen, hydroxy or oxo, or $P_2$ is a bond in which case $P_3$ is also a bond and X is $R_7$—SO_2—; or P₂ and P₃ together represent a dipeptide mimicking structure of formula III

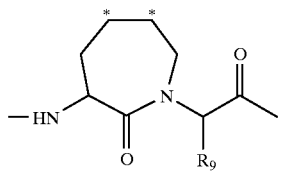

III wherein a benzene ring may be fused at the positions indicated with an asterisk and wherein $R_9$ is hydrogen or lower alkyl.

6. The serine protease inhibitor of claim 5 wherein
   X is hydrogen, lower alkyl, an acyl group, $R_7$—$SO_2$—, wherein $R_7$ is $(C_{4-10})$heterocycle, $(C_{6-14})$aryl, wherein the aryl groups may contain a heteroatom, or X is an N-protecting group;
   P₃ is a bond in which case X is $R_7$—$SO_2$—, or P₃ is selected from D-Phe, ID-Nle, D-Dpa, D-MePhe, D-1-Tiq, D-Cyk, D-Phg, D-Tic, D-Atc, D-2-Nal, D-2-Pal, D-Chg, and D-2-Nag;
   P₂ is selected from Pro, Pec, Gly, Val, Ile, 2,4-MePro, 3,3-Dmp, Ilc, Thz, Hyp, 2,2-Dmt, 5,5-Dmt, Lac, Apy, and Ac₅c, Or P₂ is a bond in which case P₃ is also a bond X is $R_7$—$SO_2$—; or
   P₂ and P₃ together represent the dipeptide mimicking structure of formula III, wherein a benzene ring may be fused at the positions indicated with an asterisk.

7. The serine protease inhibitor of claim 5, wherein the inhibitor is in the form of the acetate.

8. A compound selected from the group consisting of:
   $N^8$(D-phenylalanyl-prolyl)-3,8-diamino-6,7,8,8a-tetrahydro-8a-hydroxyimidazo[1,5a]pyridin-1(5H)-one;
   $N^8$($N^\alpha$(methyl)-D-phenylalanyl-prolyl)-3,8-diamino-6,7,8,8a-tetrahydro-8a-hydroxy imidazo[1,5a]pyridin-1(5H)-one;
   $N^8$(D-diphenylalanyl-prolyl)-3,8-diamino-6,7,8,8a-tetrahydro-8a-hydroxyimidazo[1,5a]pyridin-1(5H)-one;
   $N^8$(H-D-Phe-Ilc)-3,8-diamino-6,7,8,8a-tetrahydro-8a-hydroxyimidazo[1,5a]pyridin-1(5H)-one;
   $N^8$(H-D-MePhe-Pro)-3,8-diamino-6,7,8,8a-tetrahydro-8a-hydroxyimidazo[1,5a]pyridin-1(5H)-one;
   $N^8$(H-D-1-Tiq-Pro)-3,8-diamino-6,7,8,8a-tetrahydro-8a-hydroxyimidazo[1,5a]pyridin-1(5H)-one;
   $N^8$(H-D-Nle-Pro)-3,8-diamino-6,7,8,8a-tetrahydro-8a-hydroxyimidazo[1,5a]pyridin-1(5H)-one;
   $N^8$(Pmc-Gly)-3,8-diamino-6,7,8,8a-tetrahydro-8a-hydroxyimidazo-[1,5a]pyridin-1(5H)-one;
   $N^8$(Phth-Gly)-3,8-diamino-6,7,8,8a-tetrahydro-8a-hydroxyimidazo[1,5a]pyridin-1(5H)-one;
   $N^8$(H-D-Atc-Pro)-3,8-diamino-6,7,8,8a-tetrahydro-8a-hydroxyimidazo[1,5a]pyridin-1(5H)-one;
   $N^8$(Ac-D-Phe-Pro)-3,8-diamino-6,7,8,8a-tetrahydro-8a-hydroxyimidazo[1,5a]-pyridin-1(5H)-one;
   $N^8$(H-D-2-Nag-Pro)-3,8-diamino-6,7,8,8a-tetrahydro-8a-hydroxyimidazo[1,5a]pyridin-1(5H)-one;
   $N^8$(H-D-Phe-3,3-Dmp)-3,8-diamino-6,7,8,8a-tetrahydro-8a-hydroxyimidazo[1,5a]pyridin-1(5H)-one;
   $N^8$(H-D-Phe-2,4-MePro)-3,8-diamino-6,7,8,8a-tetrahydro-8a-hydroxyimidazo[1,5a]pyridin-1(5H)-one;
   $N^8$(H-D-Phe-2,2-Dmt)-3,8-diamino-6,7,8,8a-tetrahydro-8a-hydroxyimidazo[1,5a]pyridin-1(5H)-one;
   $N^8$(H-D-Phe-5,5-Dmt)-3,8-diamino-6,7,8,8a-tetrahydro-8a-hydroxyimidazo[1,5a]pyridin-1(5H)-one;
   $N^8$(H-D-Phe-Thz)-3,8-diamino-6,7,8,8a-tetrahydro-8a-hydroxyimidazo[1,5a]pyridin-1(5H)-one;
   $N^8$(H-D-Phe-Hyp)-3,8-diamino-6,7,8,8a-tetrahydro-8a-hydroxyimidazo[1,5a]pyridin-1(5H)-one;
   $N^8$[2-(S)[4(R)-(1,3-Dihydro-1,3-dioxo-2H-isoindol-2-yl)-1,3,4,5-tetrahydro-3-oxo-2H-2-benzazepin-2-yl]1-oxo-propyl]-3,8-diamino-6,7,8,8a-tetrahydro-8a-hydroxyimidazo[1,5a]pyridin-1(5H)-one;
   3-[[(dimethylamino)methylene]amino]-$N^8$(2-naphthylsulfonyl)-8-amino-6,7,8,8a-tetrahydro-8a-hydroxyimidazo-[1,5a]pyridin-1(5H)-one;
   $N^8$(2-naphthylsulfonyl)-3,8-diamino-6,7,8,8a-tetrahydro-8a-hydroxyimidazo[1,5a]pyridin-1(5H)-one; and
   $N^8$[$N^\alpha$(2-naphthylsulfonyl)glycyl]-3,8-diamino-6,7,8,8a-tetrahydro-8a-hydroxyimidazo[1,5a]pyridin-1(5H)-one.

9. A method of making 3,8-diamino-6,7,8,8a-tetrahydro-8a-hydroxyimidazo[1,5a]pyridin-1(5H)-one, said method comprising
   a) dissolving $N^\alpha,N^\delta$,N-tri-benzyloxycarbonyl-L-Arginine in a mixture of dichloromethane and methanol;
   b) adding 2-(1H-benzotriazol-1-yl)-1,1,3,3-tetramethyluronium tetrafluoroborate to the solution;
   c) adding triethylamine to the solution until an apparent pH of 8 is obtained;
   d) stirring the mixture at room temperature for one hour;
   e) washing the solution with water, a sodium bicarbonate solution and water;
   f) drying and evaporating to give a solid residue, and crystallizing from methanol to yield $N^\alpha,N^\delta$,N-tri-benzyloxycarbonyl-L-Arginal (Z-Arg($Z_2$)-H;
   g) adding a solution of diisobutylaluminumhydride in hexane at −78° C. to a stirred solution of Z-Arg($Z_2$)-OMe in dry dichloromethane;
   h) stirring for one hour at −78° C., after which a 20% (v/v) solution of concentrated hydrochloric acid in ethanol is added until pH 2 is obtained;
   i) extracting with dichloromethane and wash with water, a sodium bicarbonate solution, and water, drying and evaporating to give 2-acetoxy-3-(benzyloxycarbonylamino)-6-(dibenzyloxy-carbonylguanidino)hexanenitrile;
   j) adding simultaneously with stirring a solution of sodium cyanide and triethylbenzylammoniumchloride in water and acetic anhydride to a precooled solution of Z-Arg($Z_2$)-H in dichloromethane and stir for 30 minutes at 0–5° C.
   k) separating the organic layer and wash with water and aqueous brine, drying and evaporating to give a residue, which is chromatographed on silica;
   l) eluting with dichloromethane/ethyl acetate (95:5, v/v) to give a solid product 3-(benzyloxycarbonylamino)-6-(dibenzyloxycarbonyl guanidino)-2-hydroxyhexanoic acid methylester;
   m) dissolving 2-acetoxy-3-(benzyloxycarbonylamino)-6-(dibenzyloxy-carbonylguanidino) hexanenitrile in a mixture of diethylether and methanol;
   n) passing hydrogen chloride gas through the solution at −78° C. until a 3 M solution is obtained and stir for 16 hours at 5° C., then extract the mixture with dichloromethane;

o) combining the extracts and wash with water, sodium bicarbonate solution and water, and drying and evaporating to give a gum;

p) adding chromic acid slowly to a precooled solution of 3-(benzyloxycarbonylamino)-6-(dibenzyloxycarbonyl guanidino)-2-hydroxyhexanoic acid methylester in acetone and stirring for one hour at 0° C. and then pouring into ice water;

q) filtering off the precipitate, washing with water and drying in vacuo to give a white solid which is 3,8-diamino-6,7,8,8a-tetrahydro-8a-hydroxyimidazo[1,5a]pyridin-1(5H)-one;

r) adding hydrochloric acid and palladium on activated carbon to a solution of 3-(benzyloxycarbonylamino)-6-(dibenzyloxycarbonyl guanidino)-2-oxo-hexanoic acid methylester in dimethylformamide;

s) passing hydrogen gas through the solution until completion of the reaction as monitored by thin layer chromatography and filtering to remove the catalyst; and t) evaporating in vacuo to give the compound 3,8-diamino-6,7,8,8a-tetrahydro-8a-hydroxyimidazo[1,5a]pyridin-1(5H)-one.

10. A method of preparing a compound of formula II

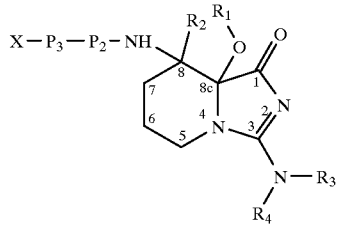

comprising condensing a compound of formula X—P$_3$—P$_3$—OH wherein

X is selected from the group consisting of hydrogen, R$_7$, R$_7$—O—C(O)—, R$_7$—C(O)—, R$_7$—SO$_2$—, —(CHR$_8$)$_m$COOR$_8$, and an N-protecting group, wherein R$_7$ is (C$_{1-12}$)alkyl or (C$_{2-12}$)alkenyl, which are unsubstituted or substituted with (C$_{3-8}$)cycloalkyl, (C$_{1-6}$)alkoxy, OH or halogen, or R$_7$ is (C$_{3-8}$)cycloalkyl, (C$_{4-10}$) heterocycle, (C$_{4-14}$)aryl, (C$_{7-15}$)aralkyl or (C$_{8-16}$)aralkenyl, which which is unsubstituted or substituted with (C$_{1-6}$)alkyl, (C$_{3-8}$)cycloalkyl, (C$_{1-6}$)alkoxy, OH or halogen and the aryl groups of which may optionally contain a heteroatom;

each group R$_6$ is independently hydrogen or has the same meaning as R$_7$;

m is 1, 2 or 3;

P$_3$ is a bond, an amino acid of the formula —NH—CH[(CH$_2$)$_p$C(O)OH]—C(O)—, p being 0, 1, 2 or 3, or an ester derivative thereof, —N(benzyl)—CH$_2$—CO—, D-Tiq, Atc, 3-Piq, 1-Piq or a D-amino acid having a hydrophobic side chain;

P$_2$ is Pro or Pec, optionally substituted with (C$_{1-4}$)alkyl, halogen, hydroxy or oxo, or an amino acid selected from Gly, Val, Ile, 2,4-MePro, 3,3-Dmp, Ilc, Thz, Hyp, 2,2-Dmt, 5,5-Dmt, Lac, Apy, Ac$_5$c, 1-Nal and 2-Nal, or P$_2$ is an amino acid of the formula —N[(C$_{3-8}$)cycloalkyl]—CH$_2$—C(O)—, the ring of which may optionally be substituted with (C$_{1-6}$)alkyl, halogen, hydroxy or oxo, or P$_2$ is a bond in which case P$_3$ is also a bond and X is R$_7$—SO$_2$—; or P$_2$ and P$_3$ together represent a dipeptide mimicking structure having formula III

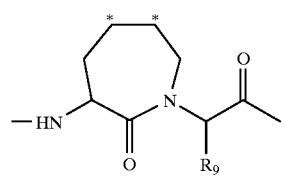

which at the positions indicated with an asterisk may be fused with a benzene ring and wherein R$_9$ is hydrogen or lower alkyl, with a 3,8-diamino-8a-hydrozyimidazo-[1,5a]pyridin-1 (5H)-one derivative of formula IV

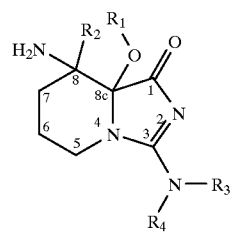

wherein R$_1$, R$_2$, R$_3$ and R$_4$ are hydrogen.

11. The method of claim 10, wherein X—P$_3$—P$_2$—OH represents a dipeptidyl group or R$_7$—SO$_2$—P$_2$—OH, or contains the dipeptide-mimicking structure of formula III,

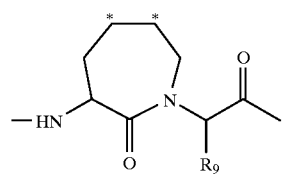

which at the positions indicated with an asterisk may be fused with a benzene ring and wherein R$_9$ is hydrogen or lower alkyl, comprising condensing by activation of the carboxylic acid function on the otherwise suitably protected structure.

12. The method of claim 10, wherein X represents R$_7$—SO$_2$ and P$_2$ and P$_3$ are a bond, said method comprising condensing by using an activated sulfonylhalide derivative, such as R$_7$—SO$_2$Cl, wherein R$_7$ is (C$_{1-12}$)alkyl or (C$_{2-12}$) alkenyl, which are unsubstituted or substituted with (C$_{3-8}$) cycloalkyl, (C$_{1-6}$)alkoxy, OH or halogen, or R$_7$ is (C$_{3-8}$) cycloalkyl, (C$_{4-10}$) heterocycle, (C$_{4-14}$)aryl, (C$_{7-15}$)aralkyl and (C$_{8-16}$)aralkenyl, which is unsubstituted or substituted with (C$_{1-6}$)alkyl, (C$_{3-8}$)cycloalkyl, (C$_{1-6}$)alkoxy, OH or halogen and wherein the aryl groups may comprise a heteroatom.

13. A method for preparing a compound of formula IV

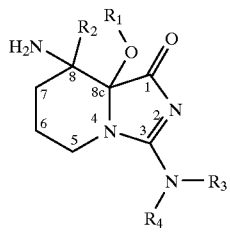

IV said method comprising adding 3-amino-6-guanidino-2-oxohexanoic acid derivatives of formula V

V wherein $R_2$ is hydrogen or lower alkyl;

and wherein $R_{10}$ and $R_{11}$ represent an N-protecting group and $R_{12}$ represents lower alkyl, by removal of the guanidino protecting groups $R_{10}$, to obtain the compound VI,

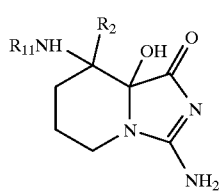

VI wherein $R_2$ and $R_{11}$ are defined as above, or may be alkylated, acylated or converted to the 8-[(amino)methylene]-amino derivative of compound VI, after which $R_{11}$ is removed.

14. A pharmaceutical composition comprising the serine protease inhibitor of claim 2 in admixture with pharmaceutically acceptable auxiliaries.

15. A pharmaceutical composition comprising the serine protease inhibitor of claim 5 in admixture with pharmaceutically acceptable auxiliaries.

16. A method for the treatment or prevention of thrombosis or other thrombin associated diseases, comprising administering an effective amount of the compound of claim 2.

17. A method for the treatment or prevention of thrombosis or other thrombin associated diseases, comprising administering an effective amount of the compound of claim 5.

* * * * *